United States Patent [19]

Sherwin et al.

[11] 4,250,344

[45] Feb. 10, 1981

[54] CRACKING PROCESS FOR STYRENE

[75] Inventors: Martin B. Sherwin, London, England; Jimmy Y. Peress, West Haven, Conn.; Kenneth J. Gwozdz, Pompton Plains, N.J.

[73] Assignee: Chem Systems Inc., New York, N.Y.

[21] Appl. No.: 954,330

[22] Filed: Oct. 25, 1978

[51] Int. Cl.³ .............................................. C07C 1/20
[52] U.S. Cl. ................................... 585/437; 585/439
[58] Field of Search ................................ 585/437, 439

[56] References Cited

U.S. PATENT DOCUMENTS 4,158,100   6/1979   Sherwin et al. ...................... 568/715

OTHER PUBLICATIONS

"Living in Twilight of the Petroleum Age", Chemical Week, Jul. 19, 1978, pp. 40-44.

Primary Examiner—Jacqueline V. Howard
Attorney, Agent, or Firm—Bert J. Lewen

[57] ABSTRACT

A process for making styrene by the cracking of beta-phenethyl acetate wherein the beta-phenethyl acetate is derived from the esterification of beta-phenethyl alcohol. The latter is derived from the homologation of benzyl alcohol-benzyl acetate mixtures. The esterification of the beta-phenethyl alcohol may be partial because it has been found that up to 20% by weight of beta-phenethyl alcohol may be fed to the cracking step and also converted to styrene. Benzyl alcohol and benzyl acetate can also be fed to the cracking step because it has been found that they are essentially inert at cracking conditions.

8 Claims, 1 Drawing Figure

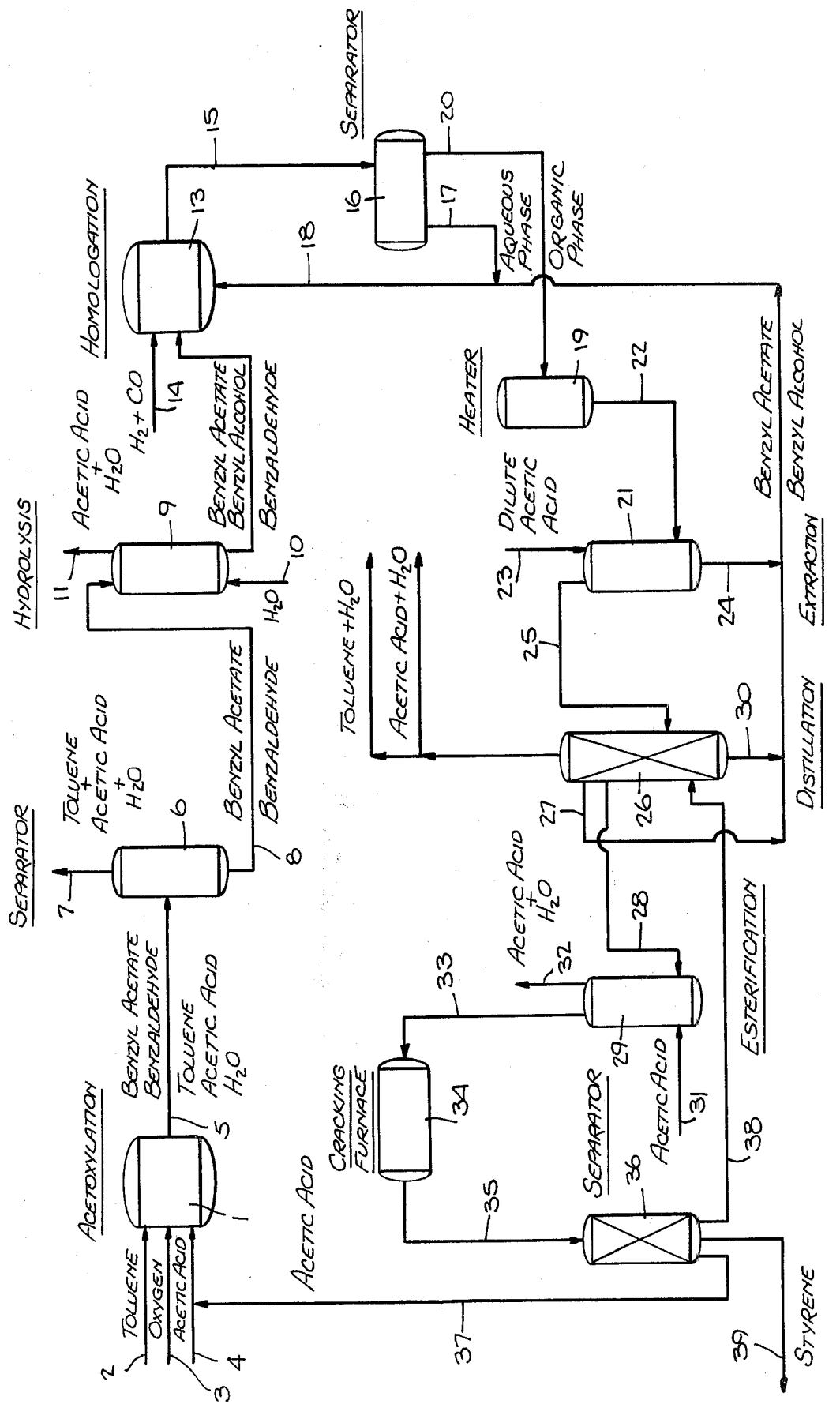

CRACKING PROCESS FOR STYRENE

BACKGROUND OF THE INVENTION

Economical processes for the preparation of styrene are of great commercial importance. Recently, it has been proposed to prepare styrene from toluene by first converting toluene to benzyl acetate or benzyl alcohol, homologating the benzyl acetate and/or benzyl alcohol to beta-phenethyl acetate and/or to beta-phenethyl acetate or the benzyl alcohol to dehydrating the beta-phenyl alcohol to form styrene. (See assignee's copending U.S. applications Ser. No. 850,209, filed Nov. 10, 1977, and Ser. No. 893,452, filed Apr. 4, 1978, and "Living in Twilight of the Petroleum Age," *Chemical Week*, July 19, 1978, pp. 40–44.) While this process is of considerable interest, a major drawback is the separation of the numerous components found in the homologation effluent. These include beta-phenethyl acetate, beta-phenethyl alcohol, benzyl alcohol, benzyl acetate, toluene, ethers, acetic acid, spent catalyst and the water of reaction. The benzyl acetate is introduced with the feedstock to the homologation, because of the difficulty of completely separating it from the benzyl alcohol. (The benzyl acetate is formed as a primary oxidation product of the toluene and is then partially hydrolyzed to a mixture consisting of benzyl alcohol and benzyl acetate.) Some of the components in the homologation effluent may be readily separated by extraction or distillation; however, others cannot. For example, the relative volatility of benzyl acetate to beta-phenethyl alcohol is less than 1.2 and that of beta-phenethyl alcohol to the beta-phenethyl acetate only about 1.1. Furthermore, these latter two compounds form an azeotrope, thus preventing their complete separation by conventional distillation.

The need to separate beta-phenethyl alcohol from beta-phenethyl acetate was considered particularly imperative because, when beta-phenethyl acetate was exposed to the dehydrating conditions used to convert the alcohol to styrene (conventionally performed in the presence of an alumina catalyst), it was found that the beta-phenethyl acetate was simultaneously converted to styrene and acetic acid. And, subsequently, the acetic acid decomposed to form undesirable products, namely, carbon dioxide and acetone. On the other hand, when pure beta-phenethyl alcohol is exposed to the cracking conditions used to form styrene from the beta-phenethyl acetate, essentially no reaction occurs.

One approach to the aforesaid problem is to attempt to hydrolyze all the beta-phenethyl acetate to the alcohol, thereby eliminating the need to separate the two components prior to the dehydration step. This, too, however, proved unsatisfactory because this hydrolysis reaction is equilibrium-limited and there is no practical means of driving the reaction to completion.

BRIEF DESCRIPTION OF THE INVENTION

In accordance with the instant invention, the mixed effluent from the homologation, after the separation of the catalyst, the low boiling components (e.g., water, acetic acid and toluene) and part of the benzyl alcohol and benzyl acetate, is at least partially esterified to convert the bulk of the beta-phenethyl components to the respective ester. The esterification proceeds rapidly because the liberated water may be readily removed overhead as a distillate. Furthermore, the esterification need not convert all of the beta-phenethyl alcohol, because it has been discovered that, in the presence of the ester, small amounts of beta-phenethyl alcohol may surprisingly also be converted to styrene at the same reaction conditions as the ester per se.

As a further embodiment of the invention, it has been discovered that the process may be further improved by eliminating the need to completely distill off the benzyl components prior to the esterification. The presence of up to twenty percent of these materials is not detrimental to the cracking process because it has been discovered that benzyl alcohol and benzyl acetate are essentially inert at the conditions at which beta-phenethyl acetate is cracked, thereby allowing less rigorous specifications for the separation of phenyl constituents from the benzyl constituents.

DETAILED DESCRIPTION OF THE INVENTION

The present invention relates to a process for the preparation of styrene from toluene wherein a mixed feed containing benzyl alcohol and a benzyl ester may be advantageously converted to styrene by the unit processes of homologation, esterification, and cracking. Particularly significant is the finding that the aforesaid unit processes may be most advantageously performed by carefully controlling the composition of the feedstocks passed to each.

By following the procedure of the instant invention, a commercially feasible process is proposed whereby difficult and costly separation steps, elaborate processing equipment, and slow reaction rates can be eliminated.

The process of the present invention is particularly adapted in a process for preparing styrene from toluene, a low-cost, readily available raw material. In such process, toluene is acetoxylated to benzyl acetate and then partially hydrolyzed to form the mixture of benzyl alcohol and benzyl acetate. It should be understood, however, that the instant invention can be applied to such benzyl components without regard to their source.

In accordance with the teaching of assignee's copending U.S. application Ser. No. 893,452, filed Apr. 4, 1978, the benzyl acetate product mixture (containing substantially the acetate) is first partially hydrolyzed to form a mixture containing from 3 to 50 wt. %, preferably from 10 to 30 wt. %, of the benzyl acetate based on the total quantity of benzyl acetate and alcohol. This latter mixture is an ideal feed to the homologation step. These steps are described in greater detail below.

It should also be apparent that other short chain carboxylic acids such as propionic, butyric, isobutyric, pentanoic and isopentanoic can be readily substituted for acetic acid in the process of the present invention.

Acetoxylation

In the acetoxylation reaction, the toluene is reacted with acetic acid and molecular oxygen. The acetic acid may be conveniently obtained as a by-product from the hydrolysis of the benzyl acetate discussed above.

The acetic acid used in the acetoxylation step must be concentrated. Where the acetoxylation is performed in the liquid stage, it is preferred that 98% acetic acid be used, while in the vapor phase reaction a concentration of 95% is sufficient. Acetic acid-water mixtures, such as obtained from the hydrolysis step, may be concentrated to 95% by simple distillation. Where higher purity is required, this step may be followed by an azeotropic distillation as is well known in the art.

The acetoxylation of toluene in the vapor phase is shown in British patent specification No. 1,328,058 and in the liquid phase in *J. Org. Chem.*, Vol. 33, No. 11 (Nov. 1968) by Bryant et al., "A Palladium-Catalyzed Synthesis of Benzyl Esters from Methyl Benzenes." The former reference shows that the acetoxylation is carried out catalytically in the vapor phase at temperatures of from 100° to 250° C., preferably 150° to 200° C., and at pressures of from 1 to 11 atm., preferably from 1 to 6 atm. The catalyst used for this reaction is palladium, preferably supported on a carrier. Co-catalysts such as bismuth and tin salts may also be used. Catalyst preparations with various catalyst additives are shown in the aforesaid references. The liquid phase process operates at temperatures of from 80° to 150° C., preferably at 100° C., and uses activated carbon as a support for the palladium.

The reaction mixture from the acetoxylation reaction is cooled to a temperature below 50° C., forming a liquid phase which consists essentially of benzyl acetate, benzaldehyde, unreacted toluene and acetic acid. The toluene and acetic acid, along with any water formed during the reaction, may be separated from the liquid phase as the distillate in a simple distillation. The toluene may be phase separated from the water and the acetic acid concentrated to form glacial acetic acid for recycle as described above. The bottoms product from this distillation, containing 90 mole %, preferably 95 mole %, benzyl acetate and up to 10 mole %, preferably not more than 5 mole %, benzaldehyde, is sent directly to the hydrolysis step.

Hydrolysis

Where benzyl acetate is used as a raw material or as an intermediate, it must first be hydrolyzed to form a preponderance of benzyl alcohol. In accordance with the present invention, this hydrolysis step is used with feedstocks containing at least 90 mole %, preferably 95 mole %, of benzyl acetate. Feedstocks containing up to 10 mole %, preferably up to 5 mole %, benzaldehyde may also be used, since benzaldehyde does not interfere with the hydrolysis step and it is beneficially fed to the homologation step. Generally, in the case of the feed to the hydrolysis reaction, not more than 10% benzaldehyde is present. On a molar basis, the ratio of water to benzyl acetate in the hydrolysis reaction is from 1:1 to 20:1, preferably from 2:1 to 8:1. The hydrolysis is catalyzed by acetic acid in accordance with a preferred embodiment of the invention. Acetic acid is readily available as a co-product from the homologation reaction, as will be described hereinafter, and is also a co-product from the hydrolysis. The use of acetic acid as the catalyst is particularly preferred because it does not require the addition of another component to the system. Catalyst concentrations of 0.005 to 0.5 mole equivalents per mole of benzyl acetate are generally used to achieve the desired reaction rate. Catalyst addition is most important at temperatures below 180° C.; otherwise, the reaction is sluggish. Temperatures for the hydrolysis are from 80° to 250° C., preferably from 130° to 220° C. Lower temperatures slow the rate of reaction, while higher temperatures lead to product decomposition. Pressure is not critical, though of course it must be sufficient to ensure that the reaction mixture is in the liquid phase. Depending on temperature, the pressure may vary from 1 atm. to about 40 atm., and preferably from 5 atm. to about 25 atm. The time for the mixture to reach equilibrium depends on the catalyst concentration, temperature, and the starting mixture. Normally, times of from 0.5 to 5 hours are sufficient.

During the hydrolysis reaction, the composition approaches the equilibrium to form a product containing from 50 to 97 mole % of benzyl alcohol, preferably from 70 to 90 mole %, based on total benzyl compounds in the product. Unconverted benzyl acetate, from about 3 to 50 mole %, preferably from 10 to 30 mole %, based on total benzyl compounds in the product, remains in the effluent. Up to 10 mole %, preferably up to 5 mole %, based on total benzyl compounds in the product, of the benzaldehyde which was present in the hydrolysis feed may be fed directly to the homologation step. Neither the benzaldehyde nor the unconverted benzyl acetate must first be removed. The only separation necessary is the separation of the organic phase from the water phase which occurs upon cooling the hydrolysis product. The water phase contains the bulk of the acetic acid plus small amounts of the three benzyl constituents. The organic phase containing the three benzyl constituents plus small amounts of acetic acid and water can be fed directly to the homologation reactor. These two phases may be separated by any conventional phase separating equipment, as is well known to those skilled in the art.

Homologation

Feedstock to the homologation step contains at least 25 mole % benzyl alcohol, preferably at least 50 mole %. From 0 to 15 mole % of benzaldehyde, preferably 0 to 10 mole %, and from 5 to 75 mole % of benzyl acetate, preferably from 5 to 50 mole %, are present. These percentages are based on the total amount of benzyl alcohol, benzaldehyde and benzyl acetate (i.e., benzyl compounds) in the feedstock.

In addition, the feedstock may also contain trace amounts of other components and advantageously 0.1 to 20 weight % of water based on the total amount of the feedstock. Preferably, from 1 to 10% of water is present. In determining the amount of water to be used, it is desirable to avoid the formation of a separate water phase. A water phase is detrimental because the catalyst is water-soluble and will be extracted from the organic reaction phase by a water phase. Greater amounts of water may be used if a coupling solvent which prevents the formation of a separate water phase is added to the reaction medium.

While a feedstock for the reaction may be obtained from the reduction and hydrolysis steps herein described, a useful feedstock may also be obtained by combining a benzyl alcohol feed with an organic recycle stream rich in benzyl acetate.

Any homologation catalyst may be used in the reaction. Most of such catalysts that are described in the foregoing references (U.S. Applns. Ser. Nos. 850,209 and 893,452) are cobalt or cobalt-promoted catalysts. These are generally present in amounts from 0.25% to 5%, calculated as moles of cobalt catalyst (as Co) to moles of benzyl compounds multiplied by 100. Over this range, variations in the amounts of catalyst are not particularly critical. As a practical matter, the amount of catalyst employed is from 1 to 3 mole %. The cobalt catalyst added to the system is selected so as to be soluble in the reaction medium. The active form of the cobalt catalyst is believed to be cobalt tetracarbonyl hydride [$HCo(CO)_4$]. This cobalt compound can be formed in situ by adding to the system a cobalt tetracarbonyl hydride-yielding compound, such as an organic salt of cobalt, particularly a water-soluble compound, e.g., cobalt acetate, cobalt formate, or cobalt propionate. Such materials are readily converted to the active cobalt form during the reaction.

Promoters may be employed in the reaction; these include a ruthenium source and an iodide source, used either alone or in combination. A ruthenium source is most conveniently added as the halide, and from 0.02 to 0.30 atoms of ruthenium, preferably from 0.04 to 0.15 atoms of ruthenium, should be present for each atom of cobalt. Ruthenium may also be introduced as a metalloorganic chemical. The iodide source may be added to the reaction system as an iodo-organic compound, such as benzyl iodide or hydrogen iodide, or as a salt form of the iodide, such as an alkali or alkaline earth metal iodide. Generally, from 0.05 to 2.0 atoms of iodide, preferably from 0.10 to 1.0 atoms of iodide, per atom of cobalt should be present. Promoted catalysts may be prepared in accordance with the teaching of U.S. Pat. No. 3,285,948.

The amount of hydrogen and carbon monoxide added in the reaction is generally in stoichiometric excess of the amount of benzyl alcohol used. As a minimum, at least stoichiometric quantities must be added and excesses up to ten times the stoichiometric amount are useful. As little as one-half mole of hydrogen to each mole of carbon monoxide may be used, and up to five moles of hydrogen to carbon monoxide may be used. The most preferred range is from 3:1 to 1:1. Sufficient carbon monoxide pressure must be applied to maintain the cobalt catalyst in its active state.

Reaction temperatures may be from 100° to 165° C., preferably from 120° to 150° C. The reaction pressure should be at least 70 atm., preferably from 70 to 500 atm., most preferably from 200 to 400 atm. Increased pressures tend to favor selectivity of the beta-phenethyl alcohol. However, the use of higher ranges of pressure is limited by practical considerations such as the selection of equipment and safety factors.

The reaction period is not critical, but should be selected so as to achieve acceptable conversions without unduly lengthening the process cycles. As a practical matter, the reaction period would range from one-half to four hours.

The effluent from the homologation reactor must be purified to concentrate the beta-phenethyl alcohol and beta-phenethyl acetate. While this purification may be readily accomplished by many schemes known to those skilled in the art, the preferred procedure is as follows. Initially, the reaction effluent is cooled and the organic phase and the aqueous phase separated. The latter, containing the water-soluble constituents of the catalyst, is recycled directly to the homologation reactor. The organic phase is thereafter heated to about 150° C. under pressure in the presence of acetic acid. The step converts the remaining cobalt constituents into water-soluble acetates. These latter compounds, along with iodide constituents, are then extracted either with water or with a dilute stream of acetic acid. The extract, preferably after the removal of excessive water by evaporation, is also recycled to the homologation reactor.

The remaining organic phase, consisting of unconverted benzyl alcohol and the benzyl ester, beta-phenethyl alcohol and the beta-phenethyl ester, toluene, dibenzyl ether, acetic acid and water, and residual catalyst constituents, is subjected to a series of distillation steps. Sequentially, toluene and water; water and acetic acid; a benzyl alcohol-benzyl ester azeotrope; and the beta-phenethyl alcohol-beta-phenethyl ester (containing some benzyl ester) fractions are removed. The residual product from the distillation, containing high boiling dibenzyl ether and the ruthenium catalyst, is recycled to the homologation. The beta-phenethyl alcohol-beta-phenethyl ester fraction is sent to the esterification step.

The separation of the benzyl constituents at this stage of the process, as described above, is desirable when the conversion of the benzyl compounds is below 80% by weight. It would be undesirable to pass large amounts of such constituents to the esterification and the cracking steps, because the presence of such additional volumes of material requires increased material handling. On the other hand, the discovery that a small amount of the benzyl constituents is not detrimental to these process steps reduces the demands on the distillation columns and effects substantial utility savings.

Esterification

The feed to the esterification step contains from 5 to 95 mole %, preferably from 30 to 70 mole %, of beta-phenethyl alcohol; from 20 to 70 mole %, preferably from 30 to 50 mole %, of beta-phenethyl ester; and from 0.1 to 20 mole %, preferably from 3 to 10 mole %, of benzyl ester and benzyl alcohol.

Any low molecular weight carboxylic acid may be used to esterify the alcohol, e.g., formic acid, acetic acid, propionic acid and butyric acid; however, it is preferred to use the same acid as is used in the acetoxylation step. Most preferably, this is acetic acid. The acid may be either a concentrated or a dilute stream containing at least one mole of acid for each mole of the alcohol. An excess of acid can be used to increase the reaction rate.

In the esterification column, temperatures in the range of from 80° to 250° C., preferably from 130° to 200° C., are used. Pressure is not critical, but rather is determined by the desired temperature and the feed composition. It is preferred that the esterification be catalyzed by acetic acid, but mineral or other acids may be used. Reaction time depends on reaction conditions. Normally, from 5 minutes to 5 hours is sufficient.

As the esterification proceeds, water is distilled off from the top of the column, thereby driving the reaction to completion. Toluene may be used to facilitate the water removal by forming an azeotrope therewith.

After the esterification is complete, the pot contains primarily beta-phenethyl ester. Benzyl ester, unconverted beta-phenethyl alcohol, and some acetic acid may also be present. While the reaction can be driven to near 100% completion, it is not necessary because applicants have discovered that up to 20% of beta-phenethyl alcohol will itself convert to styrene in the cracking step when reacted jointly with beta-phenethyl ester. Most desirably, the final product contains at least a 4:1 molar ratio of beta-phenethyl ester to beta-phenethyl alcohol.

The bottoms from the esterification column may be fed directly to the cracking step without further purification. However, if a large excess of acetic acid remains, it is desirable to separate a portion of this prior to passing the feed to the cracking reactor. The esterification may be performed batchwise or continuously.

The benzyl ester need not be separated from the feed because it is inert under cracking conditions. Benzyl alcohol is not normally present, but it can be formed under certain conditions by the hydrolysis of the benzyl ester or via the transesterification of beta-phenethyl alcohol with benzyl acetate.

Cracking Step

The primary reaction in the cracking step is the conversion of the beta-phenethyl ester to styrene and the carboxylic acid. Essentially stoichiometric yields are obtained in this thermal cracking step. The beta-phenethyl alcohol present is also converted into styrene. It is believed that the alcohol converts in situ by reacting with the acetic acid formed in the reaction to form addition benzyl ester. Thereafter the ester cracks. Any benzyl ester or benzyl alcohol in the reaction system passes through the reactor unchanged. Based on the beta-phenethyl constituents present, at least 80% by weight, preferably 90 to 95%, of the feedstock is beta-phenethyl ester. On the same basis, up to 20% by weight of beta-phenethyl alcohol and preferably from 5 to 10% by weight of beta-phenethyl alcohol is present. Up to 20% by weight and preferably up to 10% by weight of the benzyl components, namely, benzyl ester and benzyl alcohol, are also present.

The reaction is carried out at a temperature of from 450° to 650° C., preferably from 500° to 600° C. While good results are realized at atmospheric pressure, pressure of from 0.1 to 10 atm. may be employed. The reaction proceeds rapidly with contact times ranging from 0.1 to 20 seconds, preferably from 1 to 5 seconds. Diluents such as steam, nitrogen and carbon dioxide may be used if desired. Acetic acid may be present in the feed and has neither an adverse nor beneficial effect on the reaction.

Generally, the reaction takes place in a furnace containing heat-transfer tubes. After the reaction is completed, the effluent is condensed. The acetic acid by-product is recovered and recycled to the acetoxylation step. If this acetic acid contains excess water, the acetic acid is concentrated in an azeotropic drying tower. The unconverted beta-phenethyl acetate and beta-phenethyl alcohol as well as the benzyl acetate and benzyl alcohol are separated from the styrene product and sent to the benzyl-phenyl splitter which forms part of the purification system following the homologation reaction.

DESCRIPTION OF THE DRAWINGS

In order to illustrate more fully the instant invention, the attached flowsheet shows a schematic diagram of the overall process from toluene to the product styrene. As will be understood by those skilled in the art, the FIGURE is merely schematic and not intended to illustrate all of the equipment necessary for the actual process.

Initially, toluene, molecular oxygen and acetic acid are fed to the acetoxylation reactor 1 via lines 2, 3 and 4, respectively. After the reaction, the effluent containing primarily benzyl acetate, benzaldehyde, toluene, acetic acid and water exits the reactor via line 5 and is passed to separator 6. In separator 6 the toluene, acetic acid and water are removed overhead via line 7. The benzyl acetate and benzaldehyde exit via line 8 and pass to the hydrolyzer 9 wherein the water of hydrolysis is added through line 10. After the hydrolysis is completed, the aqueous phase, containing acetic acid and water, is removed via line 11; and the organic phase, containing benzyl acetate, benzaldehyde and benzyl alcohol, is removed via line 12 and fed to the homologation reactor 13. To effectuate the homologation, hydrogen and carbon monoxide are added to the homologation reactor 13 via line 14. The reactor effluent, containing water, toluene, acetic acid, benzyl alcohol and benzyl acetate, beta-phenethyl alcohol and beta-phenethyl acetate as well as components of the catalyst, is separated via line 15 and passed to separator 16. In the separator 16 the organic phase and aqueous phase are separated. The aqueous phase containing primarily soluble cobalt and sodium iodide in solution is recycled to the homologation reactor via lines 17 and 18. The organic phase passes via line 20 to the heater 19, where residual cobalt salts are converted to the acetate. The heated product thereafter passes to the extraction column 21 via line 22. In this extraction column, water or dilute acetic acid is added via line 23 to extract the additional cobalt acetate and sodium iodide. The extract is recycled to the homologation reactor 13 via lines 24 and 18. The remainder of the organic phase leaves the extractor 21 via line 25 and enters a series of distillation columns denoted by column 26. In this distillation column, a water-toluene fraction and an acetic acid-water fraction are successively removed. Thereafter, the bulk of the benzyl acetate and benzyl alcohol is removed. This latter stream is recycled via lines 27 and 18 to the homologation reactor.

The now concentrated beta-phenethyl alcohol leaves the distillation system via line 28 and passes to the esterification column 29. The bottoms product from the distillation column 26 is removed via line 30 and recycled to the homologation step via line 18. Acetic acid is added to the esterification column 29 via line 31. During the esterification, water and acetic acid are removed from the top of the column via line 32 and the esterified product passes directly to the cracking furnace 34 via line 33. In the cracking furnace 34, the beta-phenethyl ester and, as described above, the beta-phenethyl alcohol are cracked to form styrene and acetic acid. This reaction product leaves the cracking furnace 34 via line 35, is cooled, and passes to separator 36. In the separator, which is a series of distillation towers, acetic acid is removed overhead via line 37 and recycled to the acetoxylation reactor 1. If necessary, the acetic acid stream is subjected to intermediate concentration steps, not shown, prior to this recycle. The unreacted beta-phenethyl ester and beta-phenethyl alcohol and benzyl ester and benzyl alcohol are recycled from the separator 36 via line 38 to the distillation system 26. Styrene is removed from the process via line 39 and sent to storage. The particular concentrations of the constituents in the various streams shown in the figure are set forth above in connection with the description of the several reaction steps.

To more fully describe the instant invention, the following examples are set forth hereafter:

Acetoxylation

The following mixture is charged to a 500 cc. stainless steel autoclave:

| | |
|---|---:|
| Toluene | 101.61 grams |
| Acetic acid | 132.47 grams |
| Potassium acetate | 27.13 grams |
| Tin oxide (SnO) | 9.12 grams |
| Palladium acetate Pd(OAc)$_2$ | 3.99 grams |
| Carbon | 14.45 grams |
| Acetic anhydride | .47 grams |
| | 289.24 grams |

The autoclave is sealed, pressurized to 20 atm. with nitrogen, and heated to 133° C. Air is fed at an average rate of 556 cc/min. (measured at atmospheric pressure and 25° C.), for three hours. After three hours, the autoclave is cooled and depressurized. The recovered products weigh 283.9 grams (or 98.2% of the initial charge). The reactor effluent is filtered to recover the solids. The liquids analysis, by gas chromatograph, is as follows:

| Product | Wt. % |
| --- | --- |
| Toluene | 16.8 |
| Acetic acid | 40.07 |
| Benzaldehyde | 1.91 |
| Benzyl acetate | 26.13 |
| Water | 3.63 |
| Potassium acetate | 10.37 |
| Others (benzylidene diacetate and others) | 1.09 |
| Acetic anhydride | — |
| | 100.00 |

Calculation shows a conversion of toluene of 46.8% and molar selectivities of 88.2% to benzyl acetate, 9.1% to benzaldehyde and 1.9% to benzylidene diacetate. This product is distilled to first remove the water, acetic acid and toluene. The remaining product is water-washed at room temperature to remove the acetate salts and further distilled to produce 65 grams of product composed of 7 wt. % benzaldehyde and 93 wt. % benzyl acetate. The total product is distilled overhead and the diacetate remains as the residue. The remaining materials can be recycled to the oxidation step.

Hydrolysis

This benzyl acetate product from the acetoxylation step is partially hydrolyzed as follows. Water and acetic acid are added to the product in the ratios of 0.5 g./g. and 0.015 g./g., respectively. The mixture is heated to 180° C. in a glass pressure bottle under a nitrogen atmosphere. The system pressure is 15 atm. These conditions are maintained for 5 hours. Thereafter, the bottle is cooled to room temperature and two phases form. The water phase contains 9 wt. % organics and 20 wt. % acetic acid which can be reused in another hydrolysis. The organic phase accounts for 79 wt. % of the product and has the following composition:

| Component | Wt. % |
| --- | --- |
| Benzaldehyde | 5 |
| Benzyl alcohol | 38 |
| Benzyl acetate | 28 |
| Water | 12 |
| Acetic acid | 17 |

This organic phase is distilled to remove the water and acetic acid, leaving an organic product composed of 7 wt. % (8.1 mole %) benzaldehyde, 53.5 wt. % (61.3 mole %) benzyl alcohol, and 39.5 wt. % (30.1 mole %) benzyl acetate.

Along with 14 g. of water, 7 g. of cobalt octacarbonyl, 0.9 g. of ruthenium trichloride hydrate and 1.5 g. of sodium iodide, 165.6 g. of the aforesaid product are fed to a 500 cc. Hastelloy C autoclave. The autoclave is pressured to 275 atm. with synthesis gas in a $H_2/CO$ molar ratio of 1/1 and heated to 130° C. During a reaction period of 4 hours, the synthesis gas is fed at a rate of 3 liters/minute (measured at 25° C. and 1 atm.). After 4 hours, the autoclave is cooled to room temperature and depressurized. The liquid product is analyzed by gas-liquid chromatography. The percent conversions are: benzyl alcohol 27%; benzyl acetate 41.3%; and benzyl aldehyde 99.4%. The molar selectivities are: beta-phenethyl alcohol and beta-phenethyl acetate 73%; toluene 17.2%; and benzyl ether 9.8%.

Esterification

A mixture containing 288 g. (2.36 moles) of beta-phenethyl alcohol, 96 g. (0.565 mole) of beta-phenethyl acetate, 170 g. (2.83 moles) of acetic acid, and 75 g. of toluene (a mixture comparable to that obtained from the above homologation step) is fed to a reaction flask connected to a 20 plate Oldershaw column on top of which is fitted a Dean-Stark trap. The reaction flask is heated and reflux begins at 132° C. Shortly thereafter, a water-toluene azeotrope distills at a boiling point of 85° C. The water phase is separated in the Dean-Stark trap and periodically separated. At the midpoint during the distillation, 75 g. (12.5 moles) of acetic acid is added.

After about 85 g. of aqueous phase (including some acetic acid) are removed, the residue in the reaction flask is analyzed. The following results are obtained: beta-phenethyl acetate, 79.7%; beta-phenethyl alcohol, 4.7%; toluene, 7.9%; acetic acid, 5.9%; and water, 0.1%. This corresponds to a 91% esterification of the originally charged beta-phenethyl alcohol. Based on total beta-phenethyl constituents, this is equivalent to 94.4% of beta-phenethyl acetate and 5.6% beta-phenethyl alcohol.

Cracking Step

The equipment used for carrying out the cracking step consists of a Pyrex tube reactor (25 mm ID, 30 cm long). The tube is heated to the desired temperature level in an electric furnace. A traveling thermocouple is inserted into the tube to monitor the temperature along the bed. The system is fed via a preheater which first vaporizes the feed. Material is recovered by a water-cooled condenser and a product receiver. A dry ice trap after the primary receiver serves to trap any condensable material.

In the two examples described below, the cracking reaction was carried out at a temperature of about 575° C., a residence time of about 4 seconds, and a pressure of 1 atmosphere absolute.

EXAMPLE I

This example demonstrates that beta-phenethyl acetate containing limited amounts of beta-phenethyl alcohol (such as obtained by the above esterification step) can be advantageously thermally cracked to form styrene. Two mixtures are prepared. The first contains 10 wt. % beta-phenethyl alcohol and 90 wt. % beta-phenethyl acetate, and the second mixture contains 42 wt. % beta-phenethyl alcohol and 58 wt. % beta-phenethyl acetate. The following table shows the reaction conditions, product analysis, percents conversion, and percents selectivity obtained by carrying out the reaction:

TABLE I

| | Run No. 1 | Run No. 2 |
| --- | --- | --- |
| Reaction Conditions | | |
| Temperature (°C.) | 585 | 576 |
| Contact Time (secs) | 4.04 | 3.71 |
| Feed Rate (gm/hr) | 98.8 | 49.4 |

TABLE I-continued

|  | Run No. 1 | Run No. 2 |
|---|---|---|
| Reactor Volume (cc) | 49.4 | 49.4 |
| Material Balance (%) | 99.8 | 99.5 |
| Product Analysis (weight %) | | |
| Beta-phenethyl acetate | 2.0 | 2.2 |
| Beta-phenethyl alcohol | 1.5 | 38.8 |
| Styrene | 63.8 | 36.5 |
| Toluene, ethyl benzene and acetone | 0 | 0.7 |
| Acetic acid | 31.6 | 20.2 |
| Water | 0.1 | 0.4 |
| Others | 1.0 | 0.6 |
| Total | 100.0 | 99.4 |
| % Conversion (Combined) | 96.2 | 51.9 |
| Beta-phenethyl acetate conv. | 97.8 | 99.7 |
| Beta-phenethyl alcohol conv. | 85.0 | 7.4 |
| % Selectivity | | |
| Styrene | 98.8 | 96.9 |
| Toluene | 0 | 1.2 |
| Ethyl benzene | 0 | 0.9 |
| Others | 1.2 | 1.0 |
| Total | 100.0 | 100.0 |

The above data from Run 1 clearly show that, when a limited amount of beta-phenethyl alcohol is present, an extremely high selectivity to styrene is obtained. Additionally, the conversion of both compounds is extremely high: beta-phenethyl acetate, 97.8% and beta-phenethyl alcohol, 85%. In contrast, Run 2 shows a reduced selectivity to the styrene and, while a high conversion of the beta-phenethyl acetate is obtained, very little beta-phenethyl alcohol is converted. This data surprisingly reveals that the level of activity of the beta-phenethyl alcohol is quite different when amounts less than 20% are used, as contrasted to the use of greater amounts in the feedstock.

Runs under similar conditions with pure beta-phenethyl acetate as the feedstock show selectivities to styrene of 99.5% and conversions of about 94%. Hence, it can be readily seen that addition of the beta-phenethyl alcohol in limited amounts does not lead to any sacrifice in either conversion or selectivity to styrene.

EXAMPLE II

In this example, the effect of small amounts of benzyl acetate (such as is obtained from the above esterification step) on the cracking of beta-phenethyl acetate is shown. Three runs are performed. In the first run, a mixture of beta-phenethyl acetate and benzyl acetate in a molar ratio of 89/11 was reacted at a temperature of 585° C. at a 4 sec. residence time. Product analysis indicates that the beta-phenethyl acetate conversion is 98%, while the benzyl acetate conversion is only 10%. The selectivity to styrene (based on beta-phenethyl acetate and benzyl acetate consumed) was 98%. The other products formed are mainly benzaldehyde and toluene, which are recyclable to the process.

This example shows that the presence of benzyl acetate in the feed to the cracking step is not detrimental. Benzyl acetate can be used in the cracking step primarily because it is relatively inert at the level and conditions used for cracking beta-phenethyl acetate and its products are recyclable to the process, not causing a yield loss.

Having thus described our invention, what we claim and desire to protect by Letters Patent is:

1. In a process for preparing styrene by the cracking of beta-phenethyl ester, the improvement of feeding to said cracking step from 1 to 20 wt. % of beta-phenethyl alcohol in admixture with said beta-phenethyl ester.

2. In a process for the preparation of styrene, the improvement of partially esterifying beta-phenethyl alcohol derived from the homologation of benzyl alcohol so as to form an admixture of beta-phenethyl ester containing from 1 to 20 wt. % of beta-phenethyl alcohol and cracking said admixture to form styrene.

3. A process for preparing styrene which comprises: homologating a feedstock containing benzyl alcohol and from 10 to 50 wt. % of benzyl acetate withdrawing a homologation effluent containing beta-phenethyl alcohol, beta-phenethyl ester, benzyl alcohol and benzyl acetate in addition to lower and higher boiling components; separating the lower and higher boiling components from the homologation effluent, thereby forming a fraction containing primarily the beta-phenethyl alcohol, beta-phenethyl ester, benzyl alcohol and benzyl acetate; partially esterifying said fraction, while stripping off the water of reaction to form an admixture containing the benzyl compounds and from 1 to 20 wt. % of the beta-phenethyl alcohol, based on total weight of the beta-phenethyl alcohols and esters; and thereafter cracking said admixture to form styrene.

4. The process of claim 3 wherein the benzyl components are removed from the admixture prior to the cracking step.

5. In a process for preparing styrene by the cracking of beta-phenethyl acetate, the improvement of feeding to said cracking step from 1 to 20 wt. % of beta-phenethyl alcohol in admixture with said beta-phenethyl acetate.

6. In a process for the preparation of styrene, the improvement of partially esterifying beta-phenethyl-alcohol derived from the homologation of benzyl alcohol so as to form an admixture of beta-phenethyl acetate containing from 1 to 20 wt. % of beta-phenethyl alcohol and cracking said admixture to form styrene.

7. A process for preparing styrene which comprises: homologating a feedstock containing benzyl alcohol and from 10 to 50 wt. % of benzyl acetate; withdrawing a homologation effluent containing beta-phenethyl alcohol, beta-phenethyl acetate, benzyl alcohol and benzyl acetate in addition to lower and higher boiling components; separating the lower and higher boiling components from the homologation effluent, thereby forming a fraction containing primarily the beta-phenethyl alcohol, beta-phenethyl acetate, benzyl alcohol and benzyl acetate; partially esterifying said fraction, while stripping off the water of reaction to form an admixture containing the benzyl compounds and from 1 to 20 wt. % of the beta-phenethyl alcohol, based on total weight of the beta-phenethyl alcohols and esters; and thereafter cracking said admixture to form styrene.

8. The process of claim 7 wherein the benzyl components are removed from the admixture prior to the cracking step.

* * * * *